US012636365B2

(12) United States Patent
Song et al.

(10) Patent No.: US 12,636,365 B2
(45) Date of Patent: May 26, 2026

(54) MITOCHONDRION/RIBONUCLEIC ACID-TARGETED AND MIGRATABLE PHOTOSENSITIZED PROBE AND APPLICATION THEREOF

(71) Applicant: SHENZHEN INSTITUTES OF ADVANCED TECHNOLOGY, Shenzhen (CN)

(72) Inventors: Guofen Song, Shenzhen (CN); Penghui Li, Shenzhen (CN); Huaiyu Wang, Shenzhen (CN)

( * ) Notice: Subject to any disclaimer, the term of this patent is extended or adjusted under 35 U.S.C. 154(b) by 1204 days.

(21) Appl. No.: 17/435,268

(22) PCT Filed: Dec. 3, 2020

(86) PCT No.: PCT/CN2020/133586
§ 371 (c)(1),
(2) Date: Aug. 31, 2021

(87) PCT Pub. No.: WO2021/110094
PCT Pub. Date: Jun. 10, 2021

(65) Prior Publication Data

US 2022/0143184 A1 May 12, 2022

(30) Foreign Application Priority Data

Dec. 4, 2019 (CN) ......................... 201911228690.5
Nov. 30, 2020 (CN) ......................... 202011375730.1

(51) Int. Cl.
*A61K 41/00* (2020.01)
*A61K 49/00* (2006.01)
*A61P 35/00* (2006.01)

(52) U.S. Cl.
CPC ...... *A61K 41/0057* (2013.01); *A61K 49/0021* (2013.01); *A61P 35/00* (2018.01)

(58) Field of Classification Search
None
See application file for complete search history.

(56) References Cited

U.S. PATENT DOCUMENTS 10,780,090 B2 9/2020 Duffey et al.
2005/0054006 A1 3/2005 Chang et al.
2019/0248917 A1 8/2019 Chang et al.

FOREIGN PATENT DOCUMENTS

CN 103265947 8/2013
CN 104840461 8/2015
CN 106833623 6/2017
CN 107266417 10/2017
CN 107311977 11/2017
CN 108309977 7/2018
CN 108324960 7/2018
CN 111116550 5/2020
CN 111875604 11/2020

OTHER PUBLICATIONS

CN106833623_machine translation (Year: 2017).*
Lu et al (herein after "LU2"; Selective visualization of DNA G-quadruplex structures in live cells with 1-methylquinolinium-based molecular probes: The importance of indolyl moiety position towards specificity. Dyes and Pigments 143 (2017) 331-341 (Year: 2017).*
Garcia et al (Use of fluorescent probes for ROS to tease apart Type I and Type II photochemical pathways in photodynamic therapy. Methods 109 (2016) 158-166). (Year: 2016).*
International Search Report for PCT/CN2020/133586, mailed Mar. 5, 2021, 5 pages.
Written Opinion of the ISA for PCT/CN2020/133586, mailed Mar. 5, 2021, 6 pages.
Lu et al., "Selective visualization of DNA G-quadruplex structures in live cells with 1-methylquinolinium-based molecular probes the importance of indolyl moiety position towards specificity", Dyes and Pigments, Elsevier, 2017, vol. 143, pp. 331-341.

(Continued)

*Primary Examiner* — Jake M Vu
(74) *Attorney, Agent, or Firm* — Nitin Kaushik

(57) ABSTRACT

The present application discloses a mitochondrion/ribonucleic acid-targeted and migratable photosensitized probe and application thereof. The mitochondrion/ribonucleic acid-targeted and migratable photosensitized probe has a structure represented by the following Formula I:

Formula I

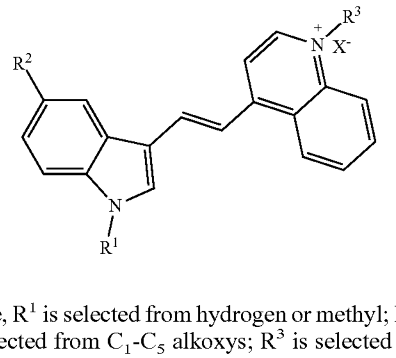

where, $R^1$ is selected from hydrogen or methyl; $R^2$ is any one of selected from $C_1$-$C_5$ alkoxys; $R^3$ is selected from methyl or hydroxymethyl; and X is selected from a halogen atom, $BF_4$, or $ClO_4$.

2 Claims, 10 Drawing Sheets

(56) References Cited

OTHER PUBLICATIONS

Rosania et al., “Combinatorial Approach to Organelle-Targeted Fluorescent Library Based on the Styryl Scaffold”, Journal of American Chemistry Soc., 2003, vol. 125, pp. 1130-1131.
Krieg et al., “N,N-Dialkylaminostyryl dyes specific and highly fuorescent substrates of peroxidase and their application in histochemistry”, Journal Mol Mist, 2008, vol. 39, pp. 169-191.
Wang et al., “Amine-substituted indole vinylquinoline as fluorescent probe for specific nucleic acids”, A Dissertation Submitted to Guangdong University of Technology for the Degree of Master of Engineering Science, School of Chemical Engineering and Light Industry Guangdong University of Technology, May 2018, 107 pages.
Kwon et al., “Mitochondria-targeting indolizino[3,2-c]quinolines as novel class photosensitizers for photodynamic anticancer activity”, Eur. J, Med Cham, Mar. 25, 2018, vol. 148, 1 page.

* cited by examiner

MITOCHONDRION/RIBONUCLEIC ACID-TARGETED AND MIGRATABLE PHOTOSENSITIZED PROBE AND APPLICATION THEREOF

CROSS-REFERENCE TO RELATED APPLICATIONS

This application is the U.S. national phase of International Application No. PCT/CN2020/133586 filed 3 Dec. 2020, and claims priority to CN Patent Application No. 201911228690.5 filed 4 Dec. 2019, and CN patent application No. 202011375730.1 filed 30 Nov. 2020, the entire contents of each of which are hereby incorporated by reference.

TECHNICAL FIELD

The present application relates to the technical field of photodynamic therapy, in particular to a mitochondrion/ribonucleic acid-targeted and migratable photosensitized probe and application thereof.

BACKGROUND

Photodynamic therapy (PDT) is a photoactivated and noninvasive treatment that adopts a photosensitizer to transform oxygen in cells into reactive oxygen species to kill the cells under light irradiation. It has been extensively applied in selective treatment of malignant diseases such as tumors. The excessive high level of reactive oxygen species during the treatment will severely damage the redox environment in cells, leading to physiological and pathological apoptosis of the cells.

A photosensitizer is critical in photodynamic therapy. However, most of traditional photosensitizers such as hematoporphyrin derivatives (HpD) and dihemorphyrin esters (DHE) are non-targeted and fail to self-monitor the efficacy in real time, resulting in the poor efficiency thereof, thereby increasing the probability of cancer recurrence. With such unsatisfactory therapeutic effect, many times of repeated treatments are required, which may not only lead to abnormal damage to normal tissues, but also enhance the drug resistance of tumor cells.

Mitochondria are closely related to the programmed cell death and canceration, and are regarded as important targets for tumor treatment. However, mitochondrial damage alone not only induces cell apoptosis, but also activates multiple anti-apoptotic pathways in the cancer cells, thereby increasing the drug resistance of cancer cells. Studies have indicated that a variety of RNAs play an important role in cancer cell proliferation and anti-apoptotic effects. However, currently, no related small-molecule probe targeting both mitochondria and RNA has been developed as photosensitizer for PDT and synchronous efficacy self-monitoring.

Technical Problems

It is an objective of embodiments of the present application to provide a mitochondrion/ribonucleic acid-targeted and migratable photosensitized probe and application thereof, in order to solve the technical problem that the existing ribonucleic acid fluorescent probes fail to have photosensitive properties, and most traditional photosensitizers fail to have the ability of targeting and synchronous efficacy self-monitoring.

SUMMARY

In view of the above-described technical problems, embodiments of the present application adopt the following technical solutions:

In a first aspect, a mitochondrion/ribonucleic acid-targeted and migratable photosensitized probe is provided, and the mitochondrion/ribonucleic acid-targeted and migratable photosensitized probe has a structure represented by the following Formula I:

Formula I

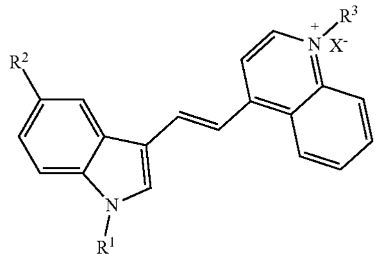

where $R^1$ is selected from hydrogen or methyl; $R^2$ is any one selected from $C_1$-$C_5$ alkoxy; $R^3$ is selected from methyl or hydroxymethyl; and X is selected from halogen atom, $BF_4$ or $ClO_4$.

In a second aspect, it is provided use of the mitochondrion/ribonucleic acid-targeted and migratable photosensitized probe as a fluorescent probe to image the distribution of ribonucleic acid and related life activities in living cells after light irradiation or in other cells with mitochondrial membrane potential loss by a non-diagnostic and non-therapeutic method.

In a third aspect, it is provided use of the mitochondrion/ribonucleic acid-targeted and migratable photosensitized probe as a targeted and migratable photosensitizer.

In a fourth aspect, it is provided use of the mitochondrion/ribonucleic acid-targeted and migratable photosensitized probe in preparing a composition for performing photodynamic therapy to kill cancer cells and synchronous efficacy monitoring.

Beneficial Effects

Advantages of the mitochondrion/ribonucleic acid-targeted and migratable photosensitized probe according to the first aspect of embodiments of the present application are summarized as follows: the provided indole quinolinium fluorescent probe is a new type of fluorescent probe molecules capable of specifically recognizing the ribonucleic acid in cells. Compared with other ribonucleic acid fluorescent probes with similar functions, the probe in the present application is characteristic in excellent photosensitivity, in particular, the probe of the present application only locates in the mitochondria in the cytoplasm of the living cells and exhibits weak fluorescence before light irradiation, while after irradiation, the probe of the present application specifically binds to the ribonucleic acid and exhibits significantly enhanced fluorescence, which is a red fluorescence different from the green fluorescence of the commercial ribonucleic acid fluorescent probe RNA-select. Meanwhile, the probe of the present application has relatively strong photostability, excellent membrane permeability and counterstaining compatibility.

Advantages of the application of the mitochondrion/ribonucleic acid-targeted and migratable photosensitized probe as a fluorescent probe according to the second aspect of embodiments of the present application are summarized as follows: the mitochondrion/ribonucleic acid-targeted and migratable photosensitized probe can be used as a fluorescent probe to image the distribution of ribonucleic acid and related life activities in living cells after light irradiation or in other cells with mitochondrial membrane potential loss, such that the probe of the present application is capable of providing simple and intuitive biological detection reagents for the physiological and pathological studies related to nucleoli and ribonucleic acid in light irradiated cells, and is also applicable for light exposure monitoring of living photophobic biological samples, thereby having extensive application and better effect.

Advantages of the application of the mitochondrion/ribonucleic acid-targeted and migratable photosensitized probe as a targeted and migratable photosensitizer according to the third aspect of embodiments of the present application are summarized as follows: the mitochondrion/ribonucleic acid-targeted and migratable photosensitized probe can be used as a targeted and migratable photosensitizer for PDT. Compared with other photosensitizers, the mitochondrion/ribonucleic acid-targeted and migratable photosensitized probe of the present application has a targeting effect. In particular, the mitochondrion/ribonucleic acid-targeted and migratable photosensitized probe of the present application can firstly target the mitochondria of the living sample cells, and only exhibits a weak fluorescent signal in the mitochondria in such condition. When mitochondria are destroyed by the reactive oxygen species generated by the photosensitized probe under light irradiation, the mitochondrial membrane potential decreases and cell apoptosis can be effectively induced. Meanwhile, the photosensitized probe is released, migrates from mitochondria and then specifically binds with the ribonucleic acid in the nucleoli and the cytoplasm of the cells, exhibiting a strong red fluorescent signal, which can be used for synchronous efficacy self-evaluation. Thereby it is realized the application of the mitochondrion/ribonucleic acid-targeted and migratable photosensitized probe as a targeted and migratable photosensitizer for PDT and synchronous efficacy monitoring.

Advantages of the application of the mitochondrion/ribonucleic acid-targeted and migratable photosensitized probe in preparing a composition for performing photodynamic therapy to kill cancer cells and synchronous efficacy monitoring according to the fourth aspect of embodiments of the present application are summarized as follows: the mitochondrion/ribonucleic acid-targeted and migratable photosensitized probe is used to prepare the composition, such that the prepared composition has targeting and migrating properties during the processes of photodynamic therapy and synchronous efficacy monitoring, thus achieving better effect.

BRIEF DESCRIPTION OF THE DRAWINGS

In order to describe the technical solutions in the embodiments of the present application more clearly, accompanying drawings used in the description of the embodiments or exemplary technologies will be briefly introduced herein below. Obviously, the accompanying drawings in the following description are only some embodiments of the present application. Other drawings may be obtained by those skilled in the art based on these drawings without creative work.

DETAILED DESCRIPTION OF THE EMBODIMENTS

Figure 1:
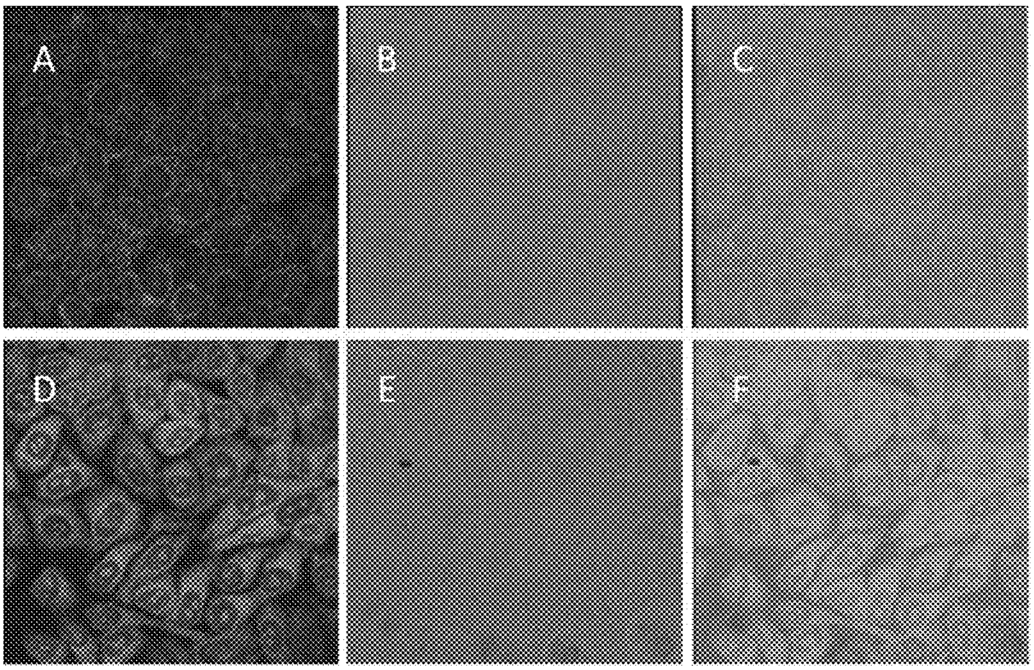
FIG. 1 is confocal fluorescent images of live HeLa cells stained with (E)-4-(2-(5-methoxy-1H-indole-3-)vinyl)-1-methylquinolinium iodide before and after light irradiation excited at 488 nm, according to Example 3 of the present application.

In order to make the objectives, technical solutions, and advantages of the present application clearer, the following further describes the present application in detail with reference to the accompanying drawings and embodiments. It should be understood that the specific embodiments described here are only used to explain the present application, and are not used to limit the present application.

It should be noted that when a component is referred to as being "fixed to" or "installed on" another component, it can be directly or indirectly on the other component. When a component is said to be "connected" to another component, it can be directly or indirectly connected to the other component. The terms "upper", "lower", "left", "right", etc. indicate the orientation or positional relationship based on the orientation or positional relationship shown in the drawings, and are only for ease of description, and do not indicate or imply the device or element referred to must have a specific orientation, be constructed and operated in a specific orientation, and therefore cannot be understood as a limitation of the present application. For those skilled in the art, the specific meaning of the above terms can be understood according to specific conditions. The terms "first" and "second" are only used for ease of description, and cannot be understood as indicating or implying relative importance or implicitly indicating the number of technical features. The meaning of "plurality" means two or more than two, unless otherwise specifically defined.

In order to illustrate the technical solutions provided by the present application, detailed descriptions are given below in conjunction with specific drawings and embodiments.

In a first aspect, embodiments of the present application provide a mitochondrion/ribonucleic acid-targeted and migratable photosensitized probe, with the structure represented by Formula I:

Formula I

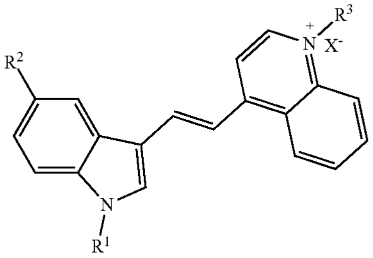

where, $R^1$ is selected from hydrogen or methyl; $R^2$ is any one selected from the group consisting of $C_1$-$C_5$ alkoxys; $R^3$ is selected from methyl or hydroxymethyl; and X is selected from a halogen atom, $BF_4$, or $ClO_4$.

The alkoxyindole quinolinium fluorescent probe provided by the present application is novel mitochondria/RNA targeted and migratable photosensitized probes. Compared with other existing ribonucleic acid fluorescent probes, the probe of the present application is characteristic in excellent photosensitivity. Compared with the conventional photosensitizers, the probe of the present application has a targeting ability. In particular, the probe of the present application can target the mitochondria of the living sample cells and exhibit a weak fluorescent signal in such condition. When mitochondria are destroyed by the reactive oxygen species produced by the photosensitized probe under the light irradiation, the mitochondrial membrane potential decreases and cell apoptosis is induced effectively. Meanwhile, the photosensitized probe molecules are released from mitochondria and specifically bind with the ribonucleic acid in the nucleoli and the cytoplasm of the cells, exhibiting a significantly enhanced fluorescent signal, which can be used for the therapy efficacy self-evaluation. In addition, the probe of the present application has relatively strong photostability, excellent membrane permeability and counterstaining compatibility.

The mitochondrion/ribonucleic acid-targeted and migratable photosensitized probe can also be referred to a photosensitive ribonucleic acid fluorescent probe for living cells, and they have the same structure represented by Formula I.

The above structural Formula I is a (2-(5-alkoxyindole-3-)vinyl) quinolinium.

In the above structural Formula I, $R^1$ is selected from hydrogen or methyl; $R^2$ is any one selected from the group consisting of $C_1$-$C_5$ alkoxys; $R^3$ is selected from methyl or hydroxymethyl; and X is selected from a halogen atom, $BF_4$, or $ClO_4$.

In the above structural Formula I, $R^2$ is any one selected from the group consisting of $C_1$-$C_3$ alkoxys, in which, the alkoxy is any one selected from the group consisting of methoxy, ethoxy, n-propoxy, and isopropoxy.

In the above structural Formula I, X is selected from a halogen atom, $BF_4$, or $ClO_4$, in which, the halogen atom is selected from an iodine atom, a bromine atom, and a chlorine atom.

In the above structural Formula I, when $R^1$ is selected from hydrogen, $R^2$ is selected from methoxy, $R^3$ is selected from methyl, and X is selected from iodine, the resulting mitochondrion/ribonucleic acid-targeted and migratable photosensitized probe is (E)-4-(2-(5-methoxy-1H-indole-3-)vinyl)-1-methylquinolinium iodide.

The mitochondrion/ribonucleic acid-targeted and migratable photosensitized probe provided in the present application is prepared by the following method for preparing the mitochondrion/ribonucleic acid-targeted and migratable photosensitized probe.

The method for preparing the mitochondrion/ribonucleic acid-targeted and migratable photosensitized probe is performed as follows: an indole-3-formaldehyde and a 4-methylquinolinium are mixed at a molar ratio of 1:(1.0-2) and dissolved in methanol/ethanol, to obtain a light yellow transparent solution, into which a small amount of piperidine is then dropped. A resulting solution is heated and refluxed for 6-12 h to produce a dark red precipitate, and then cooled to room temperature, filtered and dried in vacuum to obtain the mitochondrion/ribonucleic acid-targeted and migratable photosensitized probe.

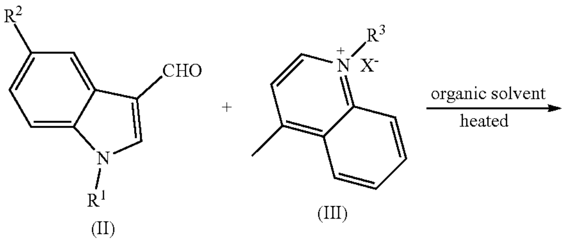

(II) (III)

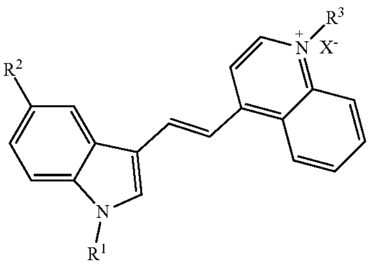

(I)

The indole-3-formaldehyde is selected from 5-methoxy-3-formylindole; the 4-methylquinolinium is selected from N-methyl-4-methylquinolinium iodide. By using 5-methoxy-3-formylindole and N-methyl-4-methylquinolinium iodide as reactants, the method for preparing the mitochondrion/ribonucleic acid targeted and migratable photosensitized probe is performed as follows:

an ethanol solution of 5-methoxy-3-formylindole and N-methyl-4-methylquinolinium iodide is prepared;

piperidine is added to the mixed ethanol solution as a catalyst, the resulting organic mixture is heated and refluxed at 85° C. for 12 h, and then cooled to room temperature to obtain dark green crystals or a dark red precipitate; and The organic precipitate is filtered, washed with a small amount of dichloromethane, and dried to obtain dark green crystals or a dark red powder. The dark green crystals and the dark red powder are all mitochondrion/ribonucleic acid-targeted and migratable photosensitized probe, which is (E)-4-(2-(5-methoxy-1H-indole-3-)vinyl)-1-methylquinolinium iodide.

In a second aspect, use of the mitochondrion/ribonucleic acid-targeted and migratable photosensitized probe as a fluorescent probe to image the distribution of ribonucleic acid and related life activities in live cells after light irradiation or in other cells with mitochondrial membrane potential loss by a non-diagnostic and non-therapeutic methods is provided.

The mitochondrion/ribonucleic acid-targeted and migratable photosensitized probe provided by embodiments of the present application can be used as a fluorescent probe to image the distribution of the ribonucleic acid and related life activities in live cells after light irradiation or in other cells with mitochondrial membrane potential loss, such that the probe of the present application is capable of providing simple and intuitive biological detection reagents for the physiological and pathological studies related to nucleoli and ribonucleic acid in cells, and is also applicable for light exposure monitoring of live photophobic biological samples, thereby having extensive application and excellent effect.

In a third aspect, use of the mitochondrion/ribonucleic acid-targeted and migratable photosensitized probe as a targeted and migratable photosensitizer is provided.

The mitochondrion/ribonucleic acid-targeted and migratable photosensitized probe can be used as a targeted and migratable photosensitizer. Compared with other photosensitizers, the mitochondrion/ribonucleic acid-targeted and migratable photosensitized probe of the present application has a targeting ability. In particular, the mitochondrion/ribonucleic acid-targeted and migratable photosensitized probe of the present application can firstly target the mitochondria of the live sample cells, and only exhibits a weak fluorescent signal in the mitochondria in such condition. When mitochondria are destroyed by the reactive oxygen species produced by the photosensitized probe molecule in photodynamic therapy, the mitochondrial membrane potential decreases and cell apoptosis is induced effectively. Meanwhile, the photosensitizer molecules are released from the mitochondria and specifically bind with the ribonucleic acid in the nucleoli and the cytoplasm of the cells, and exhibit strong red fluorescence, which can be used for synchronous efficacy self-evaluation, thereby the use of the mitochondrion/ribonucleic acid-targeted and migratable photosensitized probe as a targeted and migratable photosensitizer for synchronous efficacy monitoring is realized.

The mitochondrion/ribonucleic acid-targeted and migratable photosensitized probe is used as a targeted and migratable photosensitizer for performing photodynamic therapy to kill cancer cells and synchronous efficacy monitoring. Therefore, the (2-(5-alkoxyindole-3-)vinyl) quinolinium is provided as the targeted and migratable photosensitizer for performing photodynamic therapy to kill cancer cells and synchronous efficacy monitoring.

Since the mitochondrion/ribonucleic acid-targeted and migratable photosensitized probe (2-(5-alkoxyindole-3-)vinyl) quinolinium has a targeting ability. The mitochondrion/ribonucleic acid-targeted and migratable photosensitized probe of the present application can firstly target the mitochondria of the live sample cells, and only exhibits a weak fluorescent signal in the mitochondria. When mitochondria are destroyed by reactive oxygen species produced by the photosensitized probe molecules in photodynamic therapy, the mitochondrial membrane potential decreases and cell apoptosis is induced effectively. Meanwhile, the photosensitizer molecules are released from the mitochondria and specifically binds with the ribonucleic acid in the nucleoli and the cytoplasm of the cells, exhibiting a strong red fluorescent signal after binding, which can be used for synchronous efficacy self-evaluation, thereby the use of the mitochondrion/ribonucleic acid-targeted and migratable photosensitized probe as a targeted and migratable photosensitizer for synchronous efficacy monitoring is realized.

In use of the mitochondrion/ribonucleic acid-targeted and migratable photosensitized probe, the (2-(5-alkoxyindole-3-)vinyl) quinolinium, as the targeted and migratable photosensitizer for performing photodynamic therapy to kill cancer cells, the use method comprises:

incubating sample cells with the targeted and migratable photosensitizer, and performing light irradiation to induce generation of reactive oxygen species to destroy mitochondria of the sample cells and induce apoptosis of the living sample cells.

The mitochondrion/ribonucleic acid-targeted and migratable photosensitized probe is the (2-(5-alkoxyindole-3-)vinyl) quinolinium. The (2-(5-alkoxyindole-3-)vinyl) quinolinium is a kind of targeted photosensitizers. After being mixed with the live sample cells, the targeted photosensitizer can be located within the mitochondria in the live sample cells driven by high mitochondrial membrane potential, and only exhibits a weak fluorescence within the mitochondria, which is conducive to subsequent photodynamic therapy and synchronous efficacy monitoring.

In the step of performing the light irradiation, any light source including but not limited to a white light, a green light, and a laser is used for the light irradiation.

In the step of performing light irradiation, a white light of approximately 0.3 $W/cm^2$ is used for irradiation for a time duration between 2 and 5 min. The white light satisfying such condition is utilized to irradiate the mitochondrion/ribonucleic acid-targeted and migratable photosensitized probe, (2-(5-alkoxyindole-3-)vinyl) quinolinium, which can induce the (2-(5-alkoxyindole-3-)vinyl) quinolinium to produce reactive oxygen species to destroy mitochondria of the live sample cells, and induce apoptosis of the sample cells.

In the step of inducing the production of the reactive oxygen species by the (2-(5-alkoxyindole-3-)vinyl) quinolinium, the reactive oxygen species include: singlet oxygens, hydroxyl radicals, and other oxygenous radicals. The generation of excessive reactive oxygen species will severely damage the redox environment in the cells leading to physiological and pathological destruction of the cells, and destroy the mitochondria of the living sample cells inducing apoptosis of the sample cells.

In use of the mitochondrion/ribonucleic acid-targeted and migratable photosensitized probe, the (2-(5-alkoxyindole-3-)vinyl) quinolinium, as a targeted and migratable photosensitizer for synchronous efficacy monitoring, the use method includes:

After the live sample cells are killed by photodynamic therapy, the targeted and migratable photosensitizer (2-(5-alkoxyindole-3-)vinyl) quinolinium, migrates from the mitochondria of the sample cells and specifically binds to ribonucleic acid in cytoplasm and nucleoli, in which the photosensitizer has the migratable ability and exhibits a strong red fluorescent signal after binding with ribonucleic acid, and thereby being capable of achieving the application thereof in synchronous efficacy monitoring during the photodynamic therapy based on the significantly enhanced fluorescent signal.

When the mitochondrion/ribonucleic acid-targeted and migratable photosensitized probe, the (2-(5-alkoxyindole-3-)vinyl) quinolinium, is used as a targeted and migratable photosensitizer, the specific binding mode thereof with the ribonucleic acid is a minor groove binding mode. The minor groove binding mode refers to an external interaction between the (2-(5-alkoxyindole-3-)vinyl) quinolinium and the edge of the base pair of a major groove or a minor groove of the ribonucleic acid, which is a form of insertion and can cause slight deformation and distortion of the ribonucleic acid structure. After the binding, the (2-(5-alkoxyindole-3-)vinyl) quinolinium exhibits a strong red fluorescent signal, which is beneficial to the application of synchronous efficacy monitoring during the photodynamic therapy.

In a fourth aspect, use of a mitochondrion/ribonucleic acid-targeted and migratable photosensitized probe in preparing a composition for performing a photodynamic therapy to kill cancer cells and synchronous efficacy monitoring is provided.

In the use of the mitochondrion/ribonucleic acid-targeted and migratable photosensitized probe in preparing a composition for performing a photodynamic therapy to kill cancer cells and synchronous efficacy monitoring according to the fourth aspect of embodiments of the present application, the mitochondrion/ribonucleic acid-targeted and migratable photosensitized probe is used to prepare the composition, such that the prepared composition has targeting and migrating abilities during the processes of performing photodynamic therapy to kill the cancer cells and synchronous efficacy monitoring, thus achieving better effect.

The composition is selected from an injectable composition or an orally administrated composition.

The composition comprises a (2-(5-alkoxyindole-3-)vinyl) quinolinium and a pharmaceutically acceptable carrier, and the carrier includes, but is not limited to various pharmaceutical excipients.

The present application will be described below in conjunction with specific embodiments.

Example 1

Synthesis of (E)-4-(2-(5-methoxy-1H-indole-3-)vinyl)-1-methylquinolinium Iodide S-methoxy-3-formylindole and N-methyl-4-methylquinolinium iodide were dissolved in ethanol to obtain a light yellow transparent solution. 4 to 5 drops of piperidine were added and the solution gradually turns red. The resulting solution was refluxed for 12 h, during which a dark red solid was precipitated. After that, the resulting solution was cooled, and filtered to obtain the precipitate. The precipitate was then washed with a small amount of dichloromethane, and dark green crystals and a dark red powder were obtained. The yield was approximately 41%.

$^1H$ NMR (400 MHz, DMSO-d6), δ (ppm): 12.09 (s, 1H), 9.10 (d, J=4.0 Hz, 1H), 8.97 (d, J=8.0 Hz, 1H), 8.61 (d, J=16.0 Hz, 1H), 8.46 (d, J=4.0 Hz, 1H), 8.42 (s, 1H) 8.34 (d, J=8.0 Hz, 1H), 8.23 (d, J=4.0 Hz, 1H), 8.02 (t, J=8.0 Hz, 2H), 7.71 (d, J=4.0 Hz, 1H), 7.43 (d, J=8.0 Hz, 1H), 6.92 (dd, J=4.0, 1.7 Hz, 1H), 4.44 (s, 3H), 3.90 (s, 3H). $^{13}C$ NMR (400 MHz, DMSO-d6), δ (ppm): 155.71, 154.06, 146.87, 139.31, 138.81, 135.01, 132.45, 128.92, 127.25, 126.62, 125.82, 119.48, 114.98, 113.79, 112.96, 112.79, 102.70, 56.08, 44.30. HRMS: calculated 315.15, found 315.15.

Example 2

HeLa Cell Culture

HeLa cells were adherently cultured in a culture medium containing a 10% fetal bovine serum, in a saturated humidity incubator with 5% $CO_2$ at 37° C., and subcultured every 2-3 days.

The cells were subcultured onto the glass substrate culture dishes after growing to a logarithmic phase, which was specifically performed as follows: cells grown in the 100 mL cell culture flask were washed with a PBS solution for three times, and then digested with 1 mL 0.25% trypsin for 1 minute. After that, the trypsin was removed, a fresh culture medium was added, the cells were evenly pipetted and then counted. A cell density was controlled at a final cell concentration of $1\times10^5$ by adding certain amount of culture medium. Thereafter, the cells were seeded into culture dishes with sterile glass substrate or a glass-bottom confocal culture dish, and incubated in a 5% $CO_2$ incubator for growth. The cells grown on the slide were used in subsequent experiments.

Example 3

Observations of the HeLa Cells Stained with (E)-4-(2-(5-methoxy-1H-indole-3-)vinyl)-1-methylquinolinium Iodide The slides covered with HeLa cells prepared in Example 2 were washed three times with the PBS solution, placed in the $CO_2$ incubator, and stained in darkness for 10-120 min with a fluorescent probe solution containing 10 μM photosensitized probe (E)-4-(2-(5-methoxy-1H-indole-3-)vinyl)-1-methylquinolinium iodide, and then irradiated under a mercury lamp for 0-5 min. The following three groups of experiments were performed:

Experiment 1

(1) The cells were stained in darkness for 30 min, and then irradiated by a white light of the mercury lamp for 5 min;
(2) The cells were stained in darkness for 30 min, without light irradiation.

Experiment 2

(1) The cells were stained in darkness for 10 min.
(2) The cells were stained in darkness for 30 min.
(3) The cells were stained in darkness for 60 min.
(4) The cells were stained in darkness for 120 min.

Experiment 3

(1) The cells were stained for 30 min, and then irradiated by light at 510-560 nm for 10 seconds.

(2) The cells were stained for 30 min, and then irradiated by light at 510-560 nm for 1 minute.

(3) The cells were stained for 30 min, and then irradiated by light at 510-560 nm for 2 min.

(4) The cells were stained for 30 min, and then irradiated by light at 510-560 nm for 3 min.

(5) The cells were stained for 30 min, and then irradiated by light at 510-560 nm for 4 min.

(6) The cells were stained for 30 min, and then irradiated by light at 510-560 nm for 5 min.

The stained cells were observed under a fluorescence microscope and a confocal laser scanning microscope and the stained regions, fluorescence distributions, and intensity changes in cells were recorded.

Figure 2:
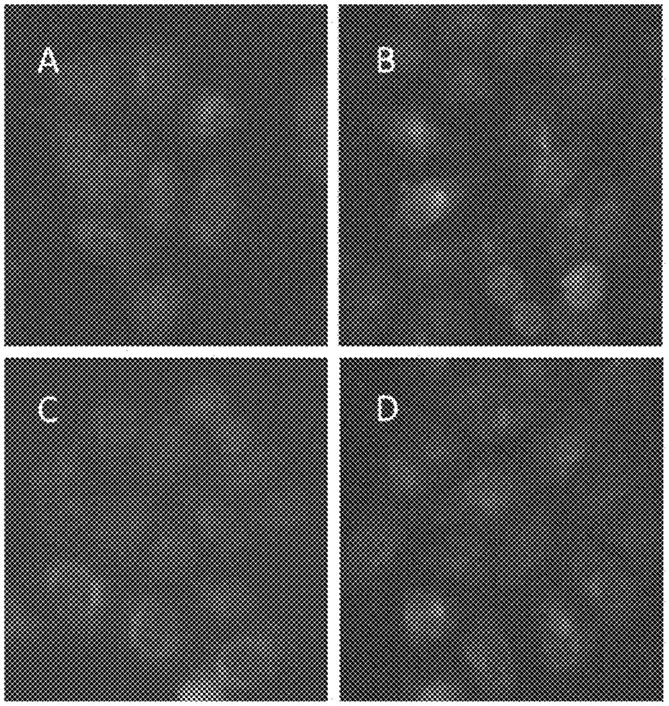
FIG. 2 is fluorescent images of live HeLa cells stained with (E)-4-(2-(5-methoxy-1H-indole-3-)vinyl)-1-methylquinolinium iodide in darkness for different durations (10-120 min) according to Example 3 of the present application.
Figure 3:
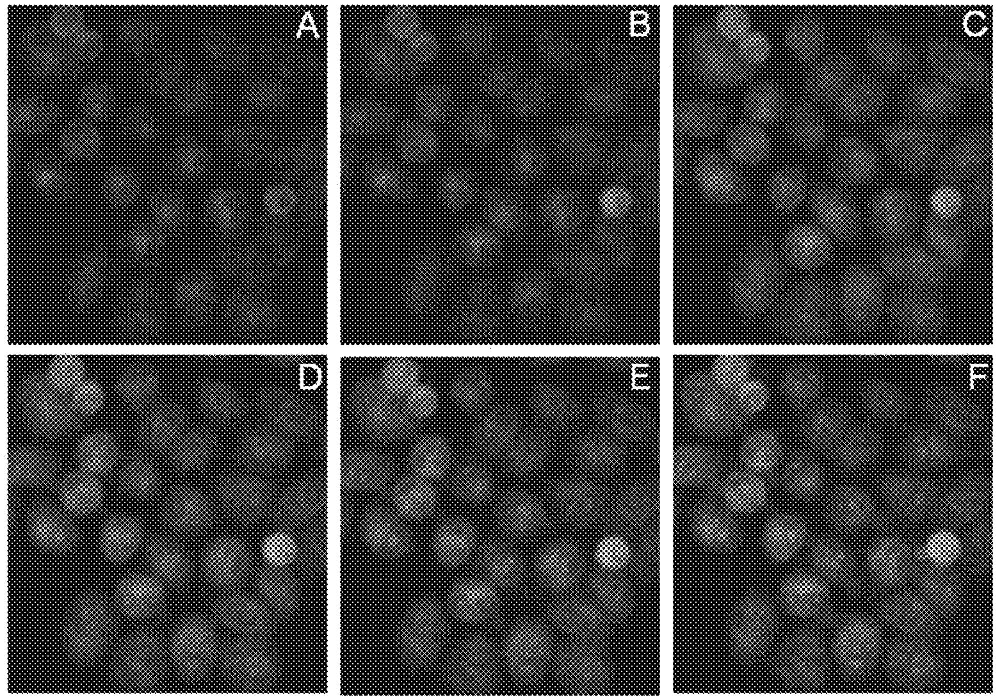
FIG. 3 is fluorescent images of live HeLa cells stained with (E)-4-(2-(5-methoxy-1H-indole-3-)vinyl)-1-methylquinolinium iodide in darkness and then irradiated by a 510-560 nm green light of a mercury lamp for different durations according to Example 3 of the present application.

Result Analysis:

The results of Experiment 1 are shown in FIG. 1, the results of Experiment 2 are shown in FIG. 2, and the results of Experiment 3 are shown in FIG. 3. The fluorescent images of FIGS. 1-3 show that live cells without light irradiation exhibit a weak red fluorescence in the cytoplasm region, but after the light irradiation, exhibit a strong red fluorescence in the cytoplasm and nucleolus regions, which undoubtedly indicates that the probe of the present application is photosensitive and can specifically image the cytoplasm and the nucleolus of the live cells after light irradiation.

FIG. 1 shows confocal fluorescent images of the stained cells under a 488 nm laser excitation in Experiment 1, before and after the light irradiation. Parts A-C of FIG. 1 are images of cells incubated in darkness (without light irradiation), Parts D-F of FIG. 1 are images after irradiated by the mercury lamp for 5 min. Part A and Part D of FIG. 1 are fluorescent images; Part B and Part E of FIG. 1 are bright-field differential interference contrast images; Part C and Part F of FIG. 1 are merged images of the left image and the middle image. The live cells without light irradiation exhibit a weak red fluorescence only in the cytoplasm region, and after light irradiation, exhibit a strong red fluorescence in the cytoplasm and nucleolus region.

FIG. 2 shows the fluorescent images of live HeLa cells stained with (E)-4-(2-(5-methoxy-1H-indole-3-)vinyl)-1-methylquinolinium iodide in darkness for different durations (10-120 min) in Experiment 2. Part A of FIG. 2 is a fluorescent image after incubation for 10 min; Part B of FIG. 2 is a fluorescent image after incubation for 30 min; Part C of FIG. 2 is a fluorescent image after incubation for 60 min; Part D of FIG. 2 is a fluorescent image after incubation for 120 min. As shown in the figures, with the incubation time increasing, the live cells stained in darkness still exhibit relatively weak red fluorescence only in the cytoplasm regions of the cells.

FIG. 3 is fluorescent images of live HeLa cells stained with (E)-4-(2-(5-methoxy-1H-indole-3-)vinyl)-1-methylquinolinium iodide in darkness and followed by irradiation with a green light at wavelength of 510-560 nm for different durations by using the mercury lamp in Experiment 3. Part A of FIG. 3 is a fluorescent image after irradiation with the 510-560 nm green light for 10 s; Part B of FIG. 3 is a fluorescent image after irradiation with the 510-560 nm green light for 1 min; Part C of FIG. 3 is a fluorescent image after irradiation with the 510-560 nm green light for 2 min; Part D of FIG. 3 is a fluorescent image after irradiation with the 510-560 nm green light for 3 min; Part E of FIG. 3 is a fluorescent image after irradiation with the 510-560 nm green light for 4 min; and Part F of FIG. 3 is a fluorescent image after irradiation with the 510-560 nm green light for 5 min. It is known from the figures that with the light irradiation time increasing, the fluorescence gradually increases, and the strong red fluorescence is distributed in the cytoplasm and the nucleolus, other than only in the cytoplasm.

Example 4

Observations of the HeLa Cells and DNase- and RNase-Treated HeLa Cells (DNase and RNase Digestion Experiments) Stained with (E)-4-(2-(5-methoxy-1H-indole-3-)vinyl)-1-methylquinolinium Iodide Preparation of fixed cells: firstly, the cover glasses (slides) covered with HeLa cells prepared in Example 2 were soaked in a 4% paraformaldehyde solution for 30 min, and then permeated with a 0.5% Triton X-100 at room temperature for 2 min to prepare fixed cells for staining.

Three groups of the above fixed cells were taken, in which, two groups were added with a 2 U/mL RNase-free DNase and a 50 μg/mL DNase-free RNase for digestion in the incubator for 2 h individually. The three groups of fixed cells were then washed three times with the PBS solution, stained with the fluorescent probe solution of 10 μM (E)-4-(2-(5-methoxy-1H-indole-3-)vinyl)-1-methylquinolinium iodide for 30 min in the $CO_2$ incubator.

The stained slides were observed under a wide-field fluorescence microscope to record the stained regions, fluorescence distribution, and intensity changes in the cells.

Figure 4:
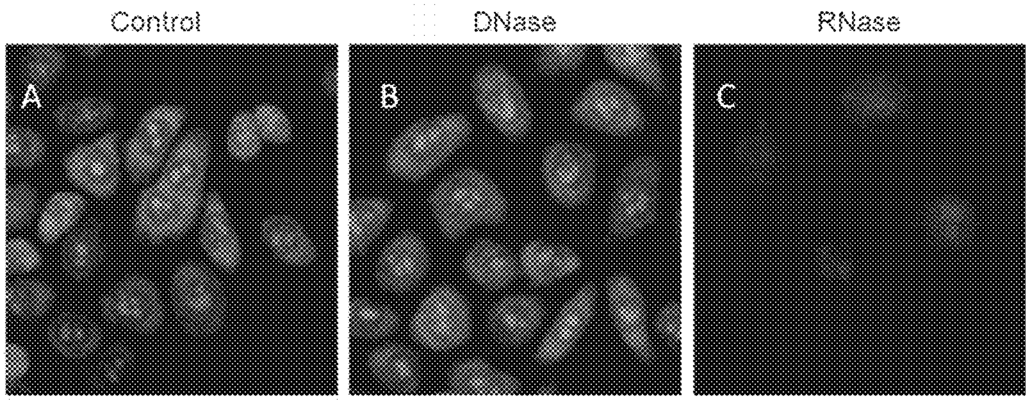
FIG. 4 is fluorescent images of HeLa cells, which are firstly fixed by paraformaldehyde solution, treated with deoxyribonuclease (DNase) and ribonuclease (RNase), respectively, stained with (E)-4-(2-(5-methoxy-1H-indole-3-)vinyl)-1-methylquinolinium iodide, and then irradiated by a 510-560 nm mercury lamp, according to Example 4 of the present application.

Result Analysis:

Results are shown in FIG. 4.

Part A of FIG. 4 is a fluorescent image of the cells in the control group (untreated group), Part B of FIG. 4 is a fluorescent image of the cells treated with DNase, and Part C of FIG. 4 is a fluorescent image of cells treated with RNase.

It can be seen from FIG. 4 that the fluorescence of the cells treated with DNase (Part B of FIG. 4) is similar to that of the control group (untreated group) (Part A of FIG. 4), and the fluorescence still locates in the cytoplasm and nucleus region, and almost no fluorescence exists in the nuclear region; the fluorescence of the cells treated with RNase 1 (Part C of FIG. 4) is much weaker than that of the control group (untreated group) (Part A of FIG. 4). Since DNase and RNase can digest and hydrolyze deoxyribonucleic acid and ribonucleic acid, respectively, it can be confirmed and verified from this view that the probe of the present application can specifically image ribonucleic acid in the fixed cells.

Example 5

Recognition Effect of (E)-4-(2-(5-methoxy-1H-indole-3-)vinyl)-1-methylquinolinium Iodide to Ribonucleic Acid and Deoxyribonucleic Acid in Solution A probe solution at concentration of 10 μM was mixed with a 120 μg/mL ribonucleic acid/deoxyribonucleic acid in PBS for 5 min, respectively, and then ultraviolet-visible absorption spectra and the fluorescence spectra under excitation at 488 nm were measured.

Figure 5:
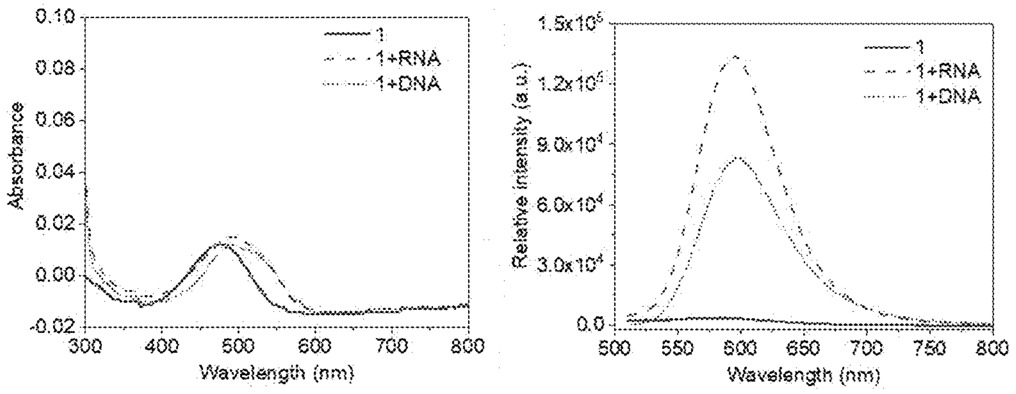
FIG. 5 is absorption spectra and fluorescence spectra of (E)-4-(2-(5-methoxy-1H-indole-3-)vinyl)-1-methylquinolinium iodide before and after interaction with ribonucleic acid (RNA) and deoxyribonucleic acid (DNA), respectively, according to Example 5 of the present application.

Result Analysis:

The results are shown in FIG. 5.

Part A of FIG. 5 shows the UV-vis absorption spectra of the probe molecule in absence/presence of ribonucleic acid/deoxyribonucleic acid; and Part B of FIG. 5 shows the fluorescence emission spectra of the probe in absence/presence of ribonucleic acid/deoxyribonucleic acid.

It can be found that the fluorescence emission peak of the probe after interacting with ribonucleic acid is around 600 nm. Compared with the probe itself, the fluorescence intensity of the probe in RNA solution increases by approximately 40 times, and is significantly stronger than the fluorescence after binding with deoxyribonucleic acid.

Example 6

Fluorescent Images of HeLa Cells Co-Stained with (E)-4-(2-(5-methoxy-1H-indole-3-)vinyl)-1-methylquinolinium Iodide and Hoechst33342

The slides covered with HeLa cells prepared in Example 2 were washed three times with the PBS solution, placed in the $CO_2$ incubator, and incubated for 30 min with 10 μM photosensitized probe (E)-4-(2-(5-methoxy-1H-indole-3-)vinyl)-1-methylquinolinium iodide, and then incubated for another 30 min with 2 μg/mL Hoechst33342.

The slides after staining were washed to remove the unbound and excess staining solution, irradiated under the green light of a mercury lamp for 5 min, and observed under a fluorescence microscope to record the stained regions, fluorescence distribution, and intensity changes in the cells.

Figure 6:
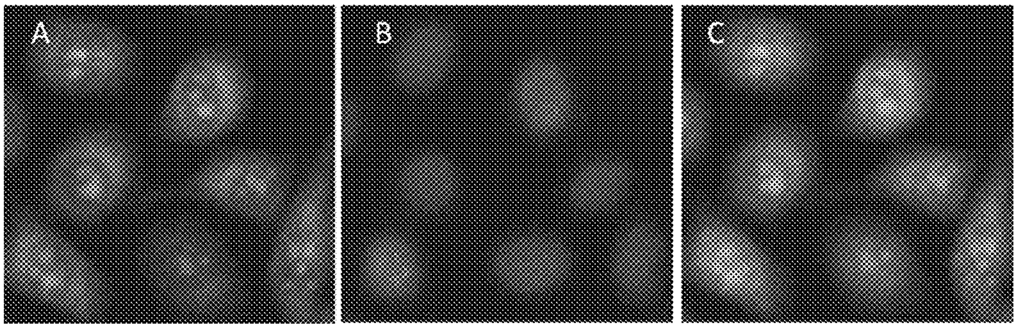
FIG. 6 is fluorescent images of HeLa cells co-stained with (E)-4-(2-(5-methoxy-1H-indole-3-)vinyl)-1-methylquinolinium iodide and the cell nucleus probe Hoechst33342 under the irradiation of the mercury lamp, according to Example 6 of the present application.

Result Analysis:

The results are shown in FIG. 6. Part A of FIG. 6 is the red fluorescent image of the probe; Part B of FIG. 6 is the blue fluorescent image of Hoechst33342; FIG. 6 (C) is an overlay image of Part A and Part B of FIG. 6, which clearly shows that red fluorescence and blue fluorescence do not affect each other, indicating that the photosensitized probe of the present application does not interfere with each other when co-stained with Hoechst 33342, and has good counterstaining compatibility.

Example 7

4T1 Cell Culture and Subcutaneous Tumor Inoculation

The 4T1 cells were cultured adherently in a culture medium containing a 10% fetal bovine serum, in a saturated humidity incubator with 5% $CO_2$ at 37° C., and subcultured every 2-3 days. After the cells have grown to the logarithmic phase, the cells were subcutaneously inoculated into the right hind leg of a nude mouse: Specifically, the overgrown cells in the T25 cell culture flask were washed with 1 mL 0.25% trypsin, and then digested with another 1 mL 0.25% trypsin for 1 to 2 min. After adding the fresh medium, the cells were evenly pipetted, counted, centrifuged and washed with PBS three times, the cell density was controlled with the added amount of PBS to make a final concentration of cells to be $1\times10^7$ per milliliter. After that the cells were inoculated subcutaneously into the right hind leg of nude mice, each with approximately $1.2\times10^6$ cells. After the tumors grow for approximately a week, the mice were used for tumor photodynamic therapy and in vivo fluorescence imaging experiments.

Example 8

Determination of the Types of Reactive Oxygen Species Generated by (E)-4-(2-(5-methoxy-1H-indole-3-)vinyl)-1-methylquinolinium Iodide in Aqueous Solutions Under Light Irradiation To determine the types of reactive oxygen species generated by (E)-4-(2-(5-methoxy-1H-indole-3-)vinyl)-1-methylquinolinium iodide, a 2 μM aqueous solution of photosensitized probe (E)-4-(2-(5-methoxy-1H-indole-3-)vinyl)-1-methylquinolinium iodide (called as photosensitized probe in Experiments 1-4) was prepared. Different reactive oxygen indicators were added to the photosensitized probe aqueous solution, and the fluorescence or absorption spectra were measured. Four experiments were conducted as follows:

Experiment 1

10 μM 2',7'-dichlorodihydrofluorescein (DCFH) was added to aqueous solutions of PBS, 2 μM photosensitized probe, 2 μM photosensitized probe of the application+0.8 mM RNA, and 2 μM Rose Bengal B (RB). These solutions were irradiated for 0-180 s with white light (300 mW/$cm^2$) of a xenon lamp with ultraviolet light filtered out, fluorescence spectra at 500-700 nm were measured under 488 nm excitation, and the fluorescence intensities at 529 nm were recorded to indicate the generation rate of all types of reactive oxygen species.

Experiment 2

50 μM ABDA was added to the aqueous solutions of PBS, 2 μM photosensitized probe, 2 μM photosensitized probe+

0.8 mM RNA, and 2 μM RB (a commercial singlet oxygen-generating photosensitizer). These solutions were irradiated for 0-6 min with the white light (300 $mW/cm^2$) of the xenon lamp, absorption spectra at 300-600 nm were measured, and the absorbance values at 378 nm were recorded to indicate the generation rate of singlet oxygen.

Experiment 3

10 μM APF was added to the aqueous solutions of PBS, 2 μM photosensitized probe, 2 μM photosensitized probe+0.8 mM RNA, 2 μM RB (a commercial singlet oxygen-generating photosensitizer). These solutions were irradiated for 0-180 s with the white light (300 $mW/cm^2$) of the xenon lamp, the fluorescence spectra at 500-700 nm were measured, and the fluorescence intensities at 514 nm were recorded to indicate the generation rate of hydroxyl radical.

Experiment 4

DMPO was added to the aqueous solutions of RNA, 2 μM photosensitized probe of the application, 2 μM photosensitized probe+0.8 mM RNA. These solutions were irradiated for 5 min by the white light (300 $mW/cm^2$) of the xenon lamp. The electron spin resonance spectra before and after irradiation were measured, and the signal intensities indicate the amount of hydroxyl radicals.

Figure 7:
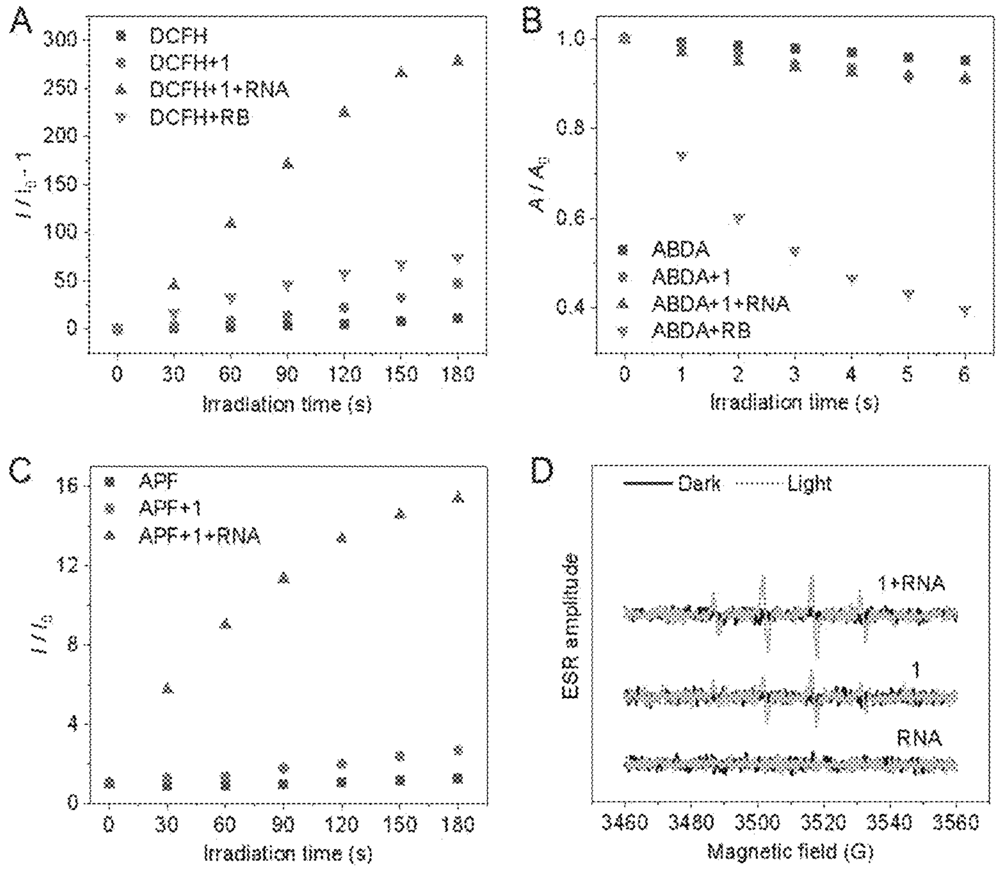
FIG. 7 is graphs showing the determination of types of reactive oxygen species generated by (E)-4-(2-(5-methoxy-1H-indole-3-)vinyl)-1-methylquinolinium iodide in an aqueous solution under light irradiation, according to Example 8 of the present application.

Result Analysis:

The experimental results of Example 8 are shown in FIG. 7. In Parts A-D of FIG. 7, "1" in the figures indicates that the 2 μM photosensitized probe (E)-4-(2-(5-methoxy-1H-indole-3-)vinyl)-1-methylquinolinium iodide is added.

The experimental results of Experiment 1 are shown in Part A of FIG. 7, which is the generation rate of all types of reactive oxygen species detected by the reactive oxygen species probe DCFH. It can be seen from Part A of FIG. 7 that the fluorescence signal of DCFH increases with the irradiation, which indicates an increase in the generation of reactive oxygen species. After the interaction with ribonucleic acid, the photosensitized probe of the present application ("DCFH+1+RNA") produces reactive oxygen species at a rate significantly higher than those of the photosensitized probe solution ("DCFH+1") and RB solution ("DCFH+RB").

The experimental results of Experiment 2 are shown in Part B of FIG. 7, which is the result of singlet oxygen generation under light irradiation detected by ABDA. It can be seen from Part B of FIG. 7 that the absorbance of ABDA, ABDA with the photosensitized probe of the present application ("ABDA+1"), ABDA with photosensitized probe and RNA ("ABDA+1+RNA") have a slight decrease with light irradiation, while the absorbance of ABDA with RB decreases much faster. The faster decrease of absorbance indicates more singlet oxygen is generated. Compared with RB, the photosensitized probe of the present application generates less singlet oxygen.

The experimental results of Experiment 3 are shown in Part C of FIG. 7, which indicate hydroxyl radicals generation under light irradiation detected by APF. It can be seen from Part C of FIG. 7 that fluorescence signal of APF increases with light irradiation, which indicates that the generation of hydroxyl radicals increases. The photosensitized probe of the present application ("APF+1") can effectively generate hydroxyl radicals, and more hydroxyl radicals are generated when the photosensitizer of the present application interacts with ribonucleic acid ("APF+1+RNA").

The experimental results of Experiment 4 are shown in Part D of FIG. 7, which is the electron spin resonance spectrum (ESR) of oxygenous radicals before and after irradiation. It can be seen from Part D of FIG. 7 that the photosensitized probe of the present application ("1") can effectively generate oxygenous radicals under the light irradiation, and more oxygenous radicals can be generated by the photosensitized probe of the present application interacted with ribonucleic acid ("1+RNA").

Example 9

Generation of Reactive Oxygen Species in HeLa Cells Treated with (E)-4-(2-(5-methoxy-1H-indole-3-)vinyl)-1-methylquinolinium iodide Before and After Photodynamic Therapy The glass-bottom cell culture dishes covered with HeLa cells prepared in Example 2 were washed three times with PBS, then incubated with 10 μM DCFH-DA in a $CO_2$ incubator in darkness for 30 min. After washed three times with PBS, the cells were then incubated with 10 μM photosensitized probe (E)-4-(2-(5-methoxy-1H-indole-3-)vinyl)-1-methylquinolinium iodide in darkness for another 30 min. The stained cells were observed under a confocal laser scanning microscope, and the fluorescence distribution and intensity changes in the cells before and after the photodynamic therapy (irradiated with mercury lamp at 510-560 nm) were recorded.

Figure 8:
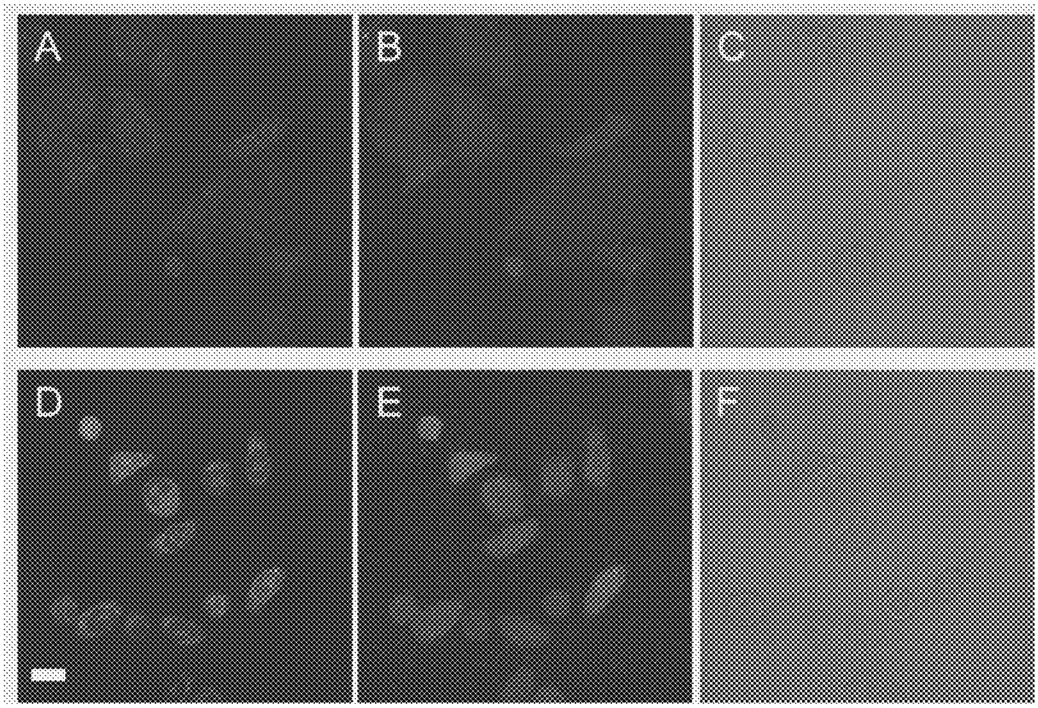
FIG. 8 is fluorescence images of the generation of reactive oxygen species in HeLa cells before and after the photodynamic therapy by (E)-4-(2-(5-methoxy-1H-indole-3-)vinyl)-1-methylquinolinium iodide according to Example 9 of the present application.

Result Analysis:

The experimental results of Example 9 are shown in FIG. 8. Parts A-C of FIG. 8 are red fluorescence of the compound prepared in Example 1, green fluorescence of DCFH-DA, and DIC images before the photodynamic therapy, respectively. It can be seen from Parts A-C of FIG. 8 that the fluorescence intensity is very weak. Parts D-F of FIG. 8 are the images of red fluorescence, green fluorescence, and DIC after irradiation for 3 min by mercury lamp, respectively. It can be seen from Part E of FIG. 8 that the intensity of green fluorescence increases remarkably after irradiation, which indicates the increase of the reactive oxygen species level in the cells.

Example 10

Observations of Colocalization of the Targeted and Migratable Photosensitized Probe (E)-4-(2-(5-methoxy-1H-indole-3-)vinyl)-1-methylquinolinium Iodide and MTG in HeLa Cells Before and After Photodynamic Therapy The glass-bottom cell culture dishes covered with HeLa cells prepared in Example 2 were washed three times with PBS, then incubated with a 1 μM MTG in a $CO_2$ incubator in darkness for 30 min. After washed three times with PBS, the cells were then incubated with was 10 μM photosensitized probe (E)-4-(2-(5-methoxy-1H-indole-3-)vinyl)-1-methylquinolinium iodide in darkness for another 30 min. The stained cells were observed under a confocal laser scanning microscope, and fluorescence distribution and intensity changes in the cells before and after the photodynamic therapy (irradiated by mercury lamp at 510-560 nm) were recorded.

Figure 9:
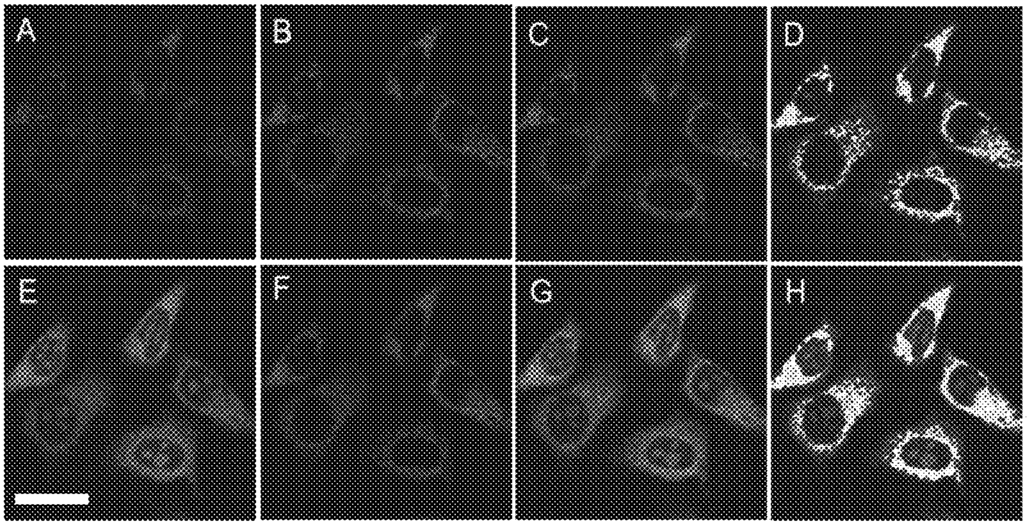
FIG. 9 is fluorescence colocalization images of the targeted and migratable photosensitizer (E)-4-(2-(5-methoxy-1H-indole-3-)vinyl)-1-methylquinolinium iodide and MitoTracker Green (MTG) in HeLa cells before and after photodynamic therapy according to Example 10 of the present application.

Result Analysis:

The experimental results of Example 10 are shown in FIG. 9. Part A of FIG. 9 is a red fluorescent image of the targeted and migratable photosensitized probe prepared in Example 1 before photodynamic therapy; Part B of FIG. 9 is a green fluorescent image of MTG before photodynamic therapy; Part C of FIG. 9 is an overlay image of the fluorescent images of the targeted and migratable photosensitized probe and MTG before photodynamic therapy; Part D of FIG. 9 is a colocalization analysis of the fluorescent images of the targeted and migratable photosensitized probe and MTG before photodynamic therapy; Part E of FIG. 9 is a fluorescent image of the targeted and migratable photosensitized probe after photodynamic therapy; Part F of FIG. 9 is a fluorescent image of MTG after photodynamic therapy; Part G of FIG. 9 is an overlay image of the fluorescent images of the targeted and migratable photosensitized probe and MTG after photodynamic therapy; and Part H of FIG. 9 is a colocalization analysis of the fluorescent images of the targeted and migratable photosensitized probe and MTG after photodynamic therapy.

By the comparative analysis of Parts A-H of FIG. 9, it can be found that the red fluorescence overlaps well with the green fluorescence of MTG before photodynamic therapy, and does not overlap well with the green fluorescence of MTG after photodynamic therapy, especially in the nucleolus regions. The colocalization of the compound prepared in Example 1 and MTG decreases obviously after photodynamic therapy, indicating that the photosensitized probe prepared in Example 1 is located in the mitochondria before photodynamic therapy, and the colocalization decrease is due to the migration of the photosensitized probe to the cytoplasm and nucleolus regions after photodynamic therapy.

Example 11

Changes of Mitochondrial Membrane Potential of HeLa Cells Treated with the Targeted and Migratable Photosensitized Probe (E)-4-(2-(5-methoxy-1H-indole-3-)vinyl)-1-methylquinolinium Iodide Before and After Photodynamic Therapy The glass-bottom cell culture dishes covered with HeLa cells prepared in Example 2 were washed three times with PBS, then incubated with JC-10 in a $CO_2$ incubator in darkness for 30 min, washed three times with PBS, and then incubated with was 10 μM photosensitized probe (E)-4-(2-(5-methoxy-1H-indole-3-)vinyl)-1-methylquinolinium iodide in darkness for another 30 min. The cells were observed under a confocal laser scanning microscope, and the fluorescence distribution and intensity changes in the cells before and after photodynamic therapy (irradiated by mercury lamp at 510-560 nm) were recorded.

Figure 10:
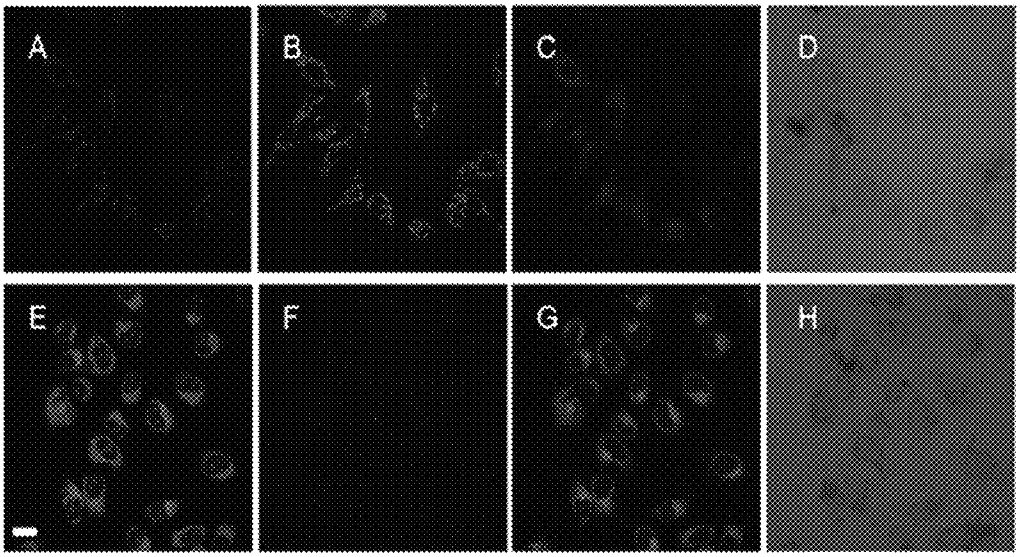
FIG. 10 is fluorescence images of mitochondrial membrane potential of HeLa cells before and after the photodynamic therapy by the targeted and migratable photosensitizer (E)-4-(2-(5-methoxy-1H-indole-3-)vinyl)-1-methylquinolinium iodide according to Example 11 of the present application.

Result Analysis:

The experimental results of Example 11 are shown in FIG. 10 which is fluorescent images of live HeLa cells co-stained by (E)-4-(2-(5-methoxy-1H-indole-3-)vinyl)-1-methylquinolinium iodide and mitochondrial membrane potential probe JC-10, before and after photodynamic therapy. Part A of FIG. 10 is a fluorescent image of the targeted and migratable photosensitized probe before photodynamic therapy; Part B of FIG. 10 is a fluorescent image of JC-10 aggregates before photodynamic therapy; Part C of FIG. 10 is a fluorescent image of JC-10 monomer before photodynamic therapy; Part D of FIG. 10 is a differential interference contrast (DIC) image before photodynamic therapy; Part E of FIG. 10 is a fluorescent image of the targeted and migratable photosensitized probe after photodynamic therapy; Part F of FIG. 10 is a fluorescent image of JC-10 aggregates after photodynamic therapy; Part G of FIG. 10 is a fluorescent image of JC-10 monomer after photodynamic therapy; and Part H of FIG. 10 is a DIC image after photodynamic therapy. It can be seen from Parts A-H of FIG. 10 that after photodynamic therapy, the fluorescence intensity of JC-10 aggregates is greatly reduced (Part F of FIG. 10), indicating that after photodynamic therapy the mitochondria membrane potential is significantly reduced, that is, the mitochondria are damaged; Meanwhile, the fluorescence intensity of the targeted and migratable photosensitized probe is enhanced (Part E of FIG. 10), indicating that the compound has the capacity of indicating the apoptosis of cells during photodynamic therapy.

Example 12

Observations of Cell Morphology of HeLa Cells Treated with (E)-4-(2-(5-methoxy-1H-indole-3-)vinyl)-1-methylquinolinium Iodide During Photodynamic Therapy The glass-bottom cell culture dishes covered with HeLa cells prepared in Example 2 were washed three times with PBS, incubated with 10 μM photosensitized probe (E)-4-(2-(5-methoxy-1H-indole-3-)vinyl)-1-methylquinolinium iodide in darkness for 30 min. The resulting stained cells and a control group without the photosensitized probe incubation were observed under a fluorescence microscope, and differential interference contrast images of the cells during the photodynamic therapy (irradiated with mercury lamp at 510-560 nm) were recorded.

Figure 11:
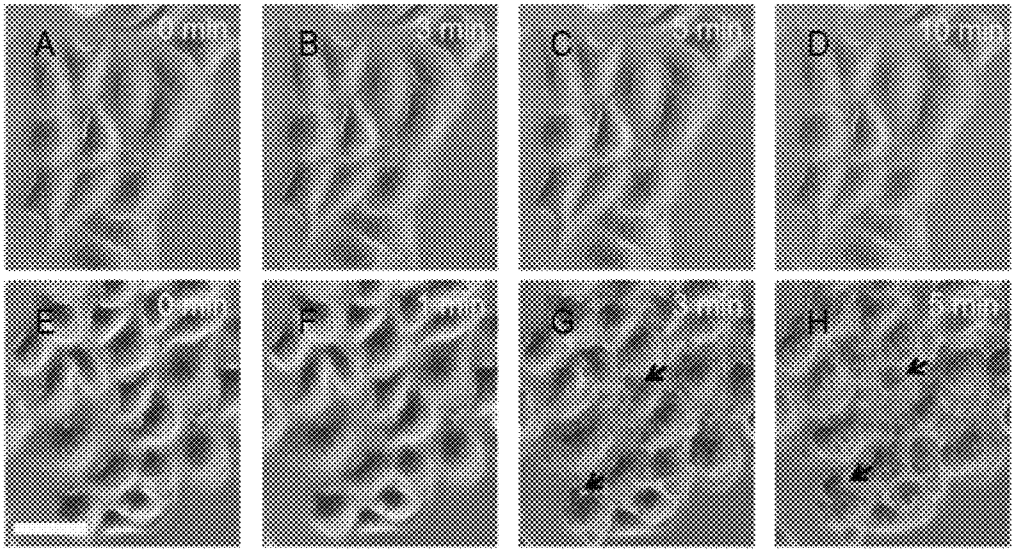
FIG. 11 is cell morphology images of live HeLa cells during photodynamic therapy treated with (E)-4-(2-(5-methoxy-1H-indole-3-)vinyl)-1-methylquinolinium iodide as the targeted and migratable photosensitizer according to Example 12 of the present application.

Result Analysis:

The experimental results of Example 12 are shown in FIG. 11. Parts A-D of FIG. 11 are the DIC images of the control group (untreated with the targeted and migratable photosensitized probe 1) at 0 min, 3 min, 5 min, and 10 min under light irradiation. Parts E-H of FIG. 11 are the DIC images of cells treated with the targeted and migratable photosensitized probe 1 of the present application at 0 min, 1 min, 3 min, and 5 min in photodynamic therapy. It can be seen from Part G of FIG. 11 that many vesicles form near cell membrane after light irradiation for 3 min, which is a symbol of cell apoptosis.

Example 13

Specific Fluorescence Recognition of (E)-4-(2-(5-methoxy-1H-indole-3-)vinyl)-1-methylquinolinium Iodide for Ribonucleic Acid in a Solution 2 μM (E)-4-(2-(5-methoxy-1H-indole-3-)vinyl)-1-methylquinolinium iodide was mixed with various biomolecules in PBS. After interaction for 5 min, the fluorescence spectra under excitation at 500 nm were measured, and the fluorescence intensities at 600 nm were recorded. Biomolecules include: Ribonucleic acid (RNA, 1.6 mM), deoxyribonucleic acid (DNA, 1.6 mM), amino acids (10 mM), hydrogen peroxide (10 mM), and metal ions (10 mM); in which, the amino acids include: Glutathione (GSH), homocysteine (Hcy), cysteine (Cys), glycine (AAA), alanine (Ala), norvaline (Nor), glutamate (Glu), histidine (his), isoleucine (Iso), leucine (Leu), methionine (Met), phenylalanine (Phe), proline (Pro), serine (Ser), threonine (Thr), tryptophan (Try), and tyrosine (Tyr); and the metal ions include: $Ca^{2+}$, $Fe^{3+}$, $Mg^{2+}$, and $Zn^{2+}$.

Figure 12:
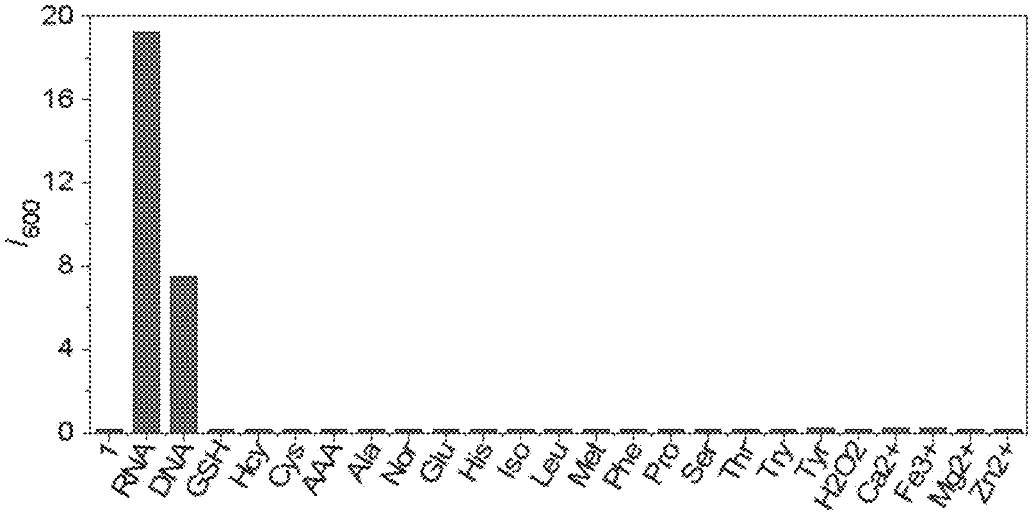
FIG. 12 is a graph showing comparisons in fluorescence recognition of (E)-4-(2-(5-methoxy-1H-indole-3-)vinyl)-1-methylquinolinium iodide for various biomolecules in aqueous solution according to Example 13 of the present application.

Result Analysis:

The experimental results of Example 13 are shown in FIG. 12. Compared with the targeted and migratable photosensitized probe itself (1), the fluorescence intensity of the probe after binding with ribonucleic acid has increased by more than 100 times, which is significantly stronger than that of the probe after binding with deoxyribonucleic acid. However, it has no obvious fluorescence response to other biomolecules.

Example 14

Specific Binding Mode of (E)-4-(2-(5-methoxy-1H-indole-3-)vinyl)-1-methylquinolinium Iodide with Ribonucleic Acid in Solution 10 μM (E)-4-(2-(5-methoxy-1H-indole-3-)vinyl)-1-methylquinolinium iodide was mixed with ribonucleic acid and deoxyribonucleic acid in PBS for 5 min, and the circular dichroism spectra were measured.

Figure 13:
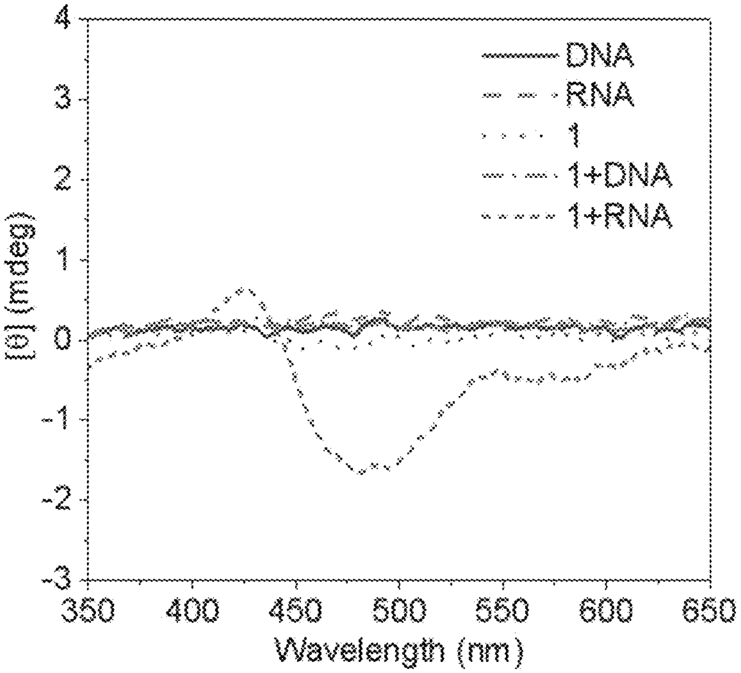
FIG. 13 is circular dichroism spectra of (E)-4-(2-(5-methoxy-1H-indole-3-)vinyl)-1-methylquinolinium iodide in presence of ribonucleic acid and deoxyribonucleic acid according to Example 14 of the present application.

Result Analysis:

The Result analysis of Example 14 is shown in FIG. 13. The spectrum of (E)-4-(2-(5-methoxy-1H-indole-3-)vinyl)-1-methylquinolinium iodide ("1") exhibits no obvious change after being mixed with DNA ("1+DNA"), but exhibits negative Cotton effect after being mixed with RNA ("1+RNA"), indicating that the binding mode of the interaction between (E)-4-(2-(5-methoxy-1H-indole-3-)vinyl)-1-methylquinolinium iodide with ribonucleic acid is minor groove binding.

Example 15

Statistical Comparison of Fluorescence Intensity in HeLa Cells Treated with (E)-4-(2-(5-methoxy-1H-indole-3-)vinyl)-1-methylquinolinium Iodide Before and After Photodynamic Therapy Three groups of HeLa cells prepared in Example 2 were washed three times with PBS. The first group was used as a blank control, and the second group was incubated with 10 μM photosensitized probe (E)-4-(2-(5-methoxy-1H-indole-3-)vinyl)-1-methylquinolinium iodide for 30 min in darkness, and then washed three times with PBS. The third group was firstly incubated with 10 μM photosensitized probe (E)-4-(2-(5-methoxy-1H-indole-3-)vinyl)-1-methylquinolinium iodide for 30 min in darkness, washed three times with PBS, and then irradiated with the white light of a xenon lamp (ultraviolet light filtered out) for photodynamic therapy for 5 min. The three groups of cells were digested in darkness and dispersed in PBS, and the number of cells and their fluorescence intensities are recorded and analyzed by flow cytometry was.

Figure 14:
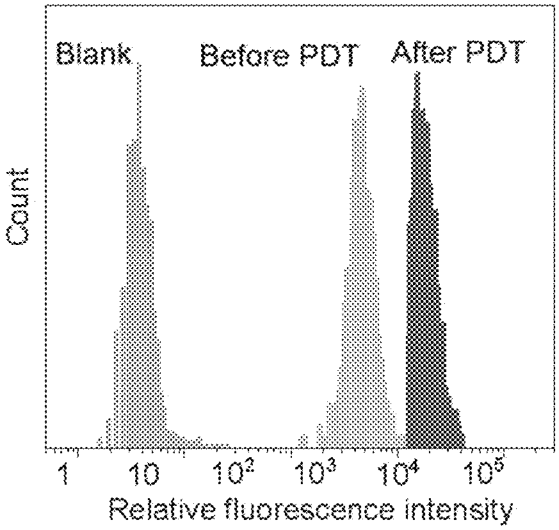
FIG. 14 is a flow cytometry fluorescence intensity statistics graph of live HeLa cells treated with (E)-4-(2-(5-methoxy-1H-indole-3-)vinyl)-1-methylquinolinium iodide before and after photodynamic therapy according to Example 15 of the present application.

Result Analysis:

The experimental results of Example 15 are shown in FIG. 14. It can be seen from FIG. 14 that compared with the group without photodynamic therapy (the second group), the fluorescence intensity of the cells after photodynamic therapy has enhanced significantly, implying that the photosensitized probe of the present application has the potential to synchronously monitor the efficacy by fluorescence imaging during in vivo photodynamic therapy.

Example 16

Photodynamic Therapy Efficiency of (E)-4-(2-(5-methoxy-1H-indole-3-)vinyl)-1-methylquinolinium Iodide to HeLa Cells The HeLa cells prepared in Example 2 were incubated in a 96-well plate with $1 \times 10^4$ cells per well. After growing adherently overnight, the cells were incubated with various concentrations of (E)-4-(2-(5-methoxy-1H-indole-3-)vinyl)-1-methylquinolinium iodide in darkness for various times. The cell viability was determined by the MTT method to determine the dark toxicity of the probe. The cells were incubated with various concentrations of (E)-4-(2-(5-methoxy-1H-indole-3-)vinyl)-1-methylquinolinium iodide for 30 min in darkness, washed three times with PBS, and subjected to photodynamic therapy under a white light of the xenon lamp (ultraviolet light filtered out) for 5 min, and then the cell viability was determined by the MTT method to determine the photodynamic therapy efficiency of the probe.

Figure 15:
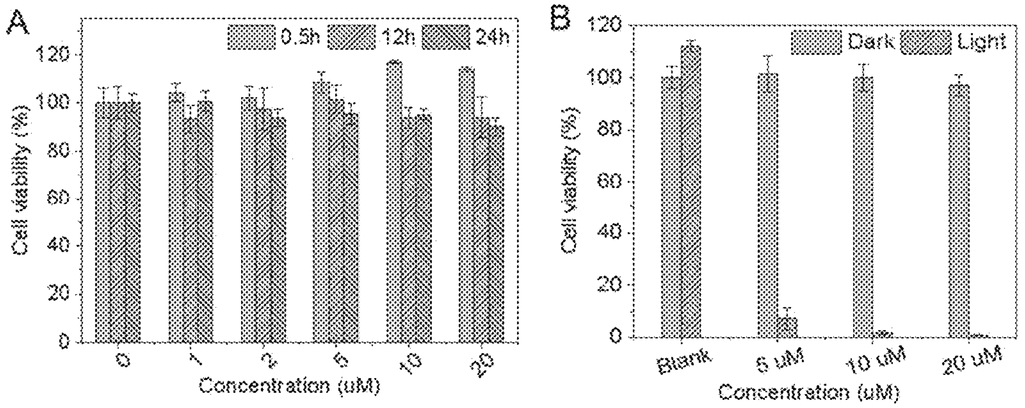
FIG. 15 is graphs showing dark toxicity of (E)-4-(2-(5-methoxy-1H-indole-3-)vinyl)-1-methylquinolinium iodide towards live HeLa cells and cell viability before and after photodynamic therapy, according to Example 16 of the present application.

Result Analysis:

The experiment results of Example 16 are shown in FIG. 15. Part A of FIG. 15 shows the viability of the living cells after incubation with the probe at the concentrations of 0-20 μM. The cell viability is still close to 100% after incubation for 24 h, indicating that the dark toxicity of the photosensitized probe drug is very low and negligible. Part B of FIG. 15 shows the cell viability before and after photodynamic therapy after incubation with the probe at concentrations of 5-20 μM in darkness. The cell viability after photodynamic therapy is greatly reduced, indicating the excellent photodynamic therapy efficiency of the probe of the present application.

Example 17

Fluorescence Monitoring by (E)-4-(2-(5-methoxy-1H-indole-3-)vinyl)-1-methylquinolinium Iodide During and after Photodynamic Therapy for 4T1 Tumor Implanted Nude Mice and the Therapy Efficacy The nude mouse tumor models prepared in Example 7 were divided into three groups for intratumor injection of drugs, with a dosage of 50 μL (1 mM) per tumor volume 100 mm³. The first group was injected with PBS and performed with light irradiation treatment; the second group was injected with (E)-4-(2-(5-methoxy-1H-indole-3-)vinyl)-1-methylquinolinium iodide and fed in darkness, and the third group was injected with (E)-4-(2-(5-methoxy-1H-indole-3-)vinyl)-1-methylquinolinium iodide and performed with light irradiation treatment.

Figure 16:
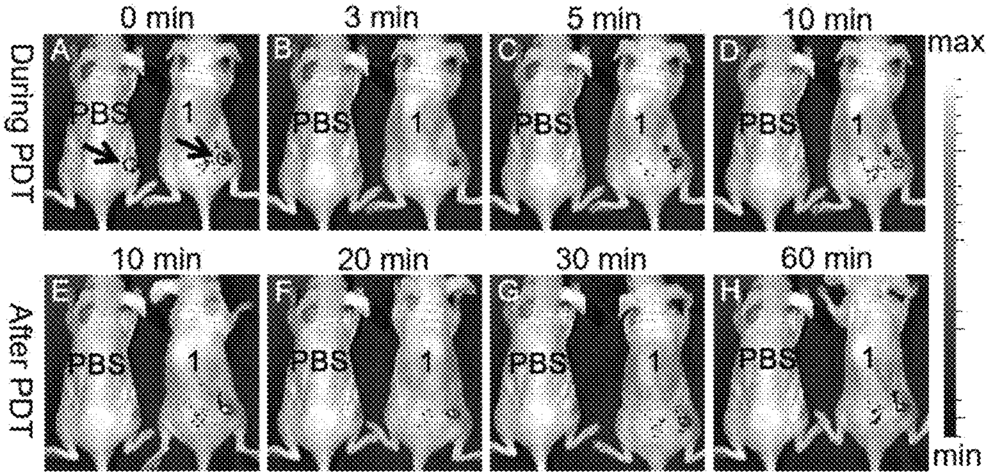
FIG. 16 is in vivo fluorescence imaging of 4T1 cell subcutaneous tumor in nude mice of the PBS control group and those administered with (E)-4-(2-(5-methoxy-1H-indole-3-)vinyl)-1-methylquinolinium iodide, at 0-10 min during photodynamic therapy and at 10-60 min after the photodynamic therapy, provided by Example 17.
Figure 17:
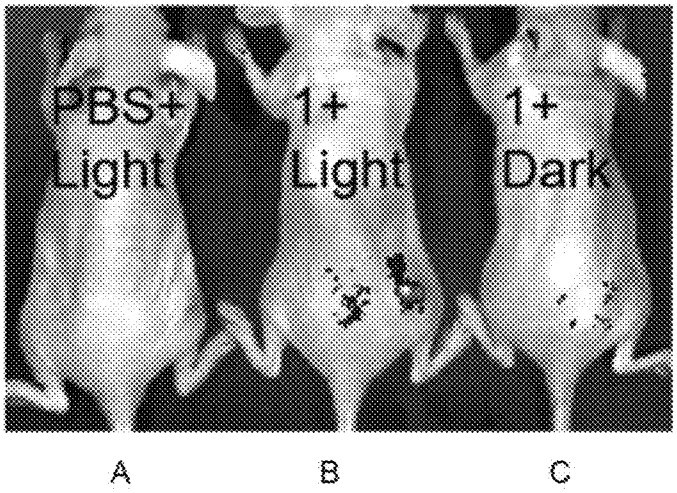
FIG. 17 is in vivo fluorescence imaging of nude mice of the PBS blank control group, the group after photodynamic therapy, and those with drug administration but without photodynamic therapy, provided by Example 17.
Figure 18:
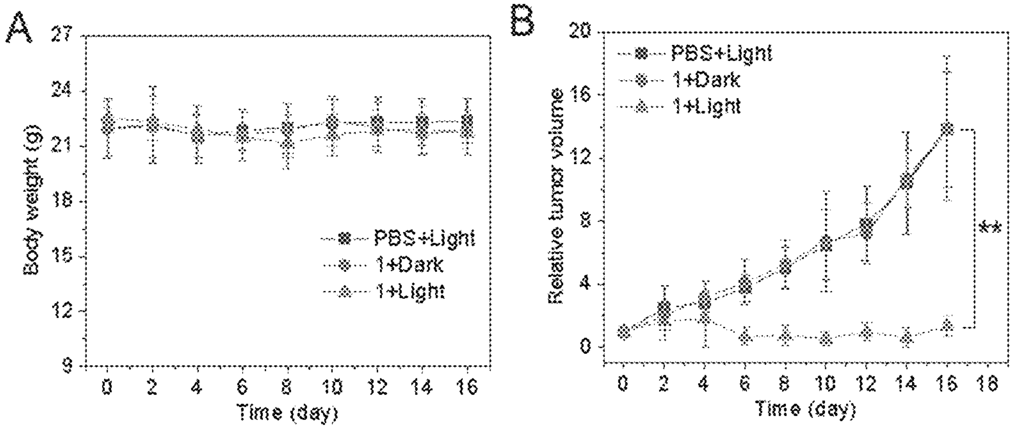
FIG. 18 is body weight curves and tumor growth curves of nude mice after photodynamic therapy of 4T1 cell subcutaneous tumor in nude mice by (E)-4-(2-(5-methoxy-1H-indole-3-)vinyl)-1-methylquinolinium iodide, provided by Example 17.
Figure 19:
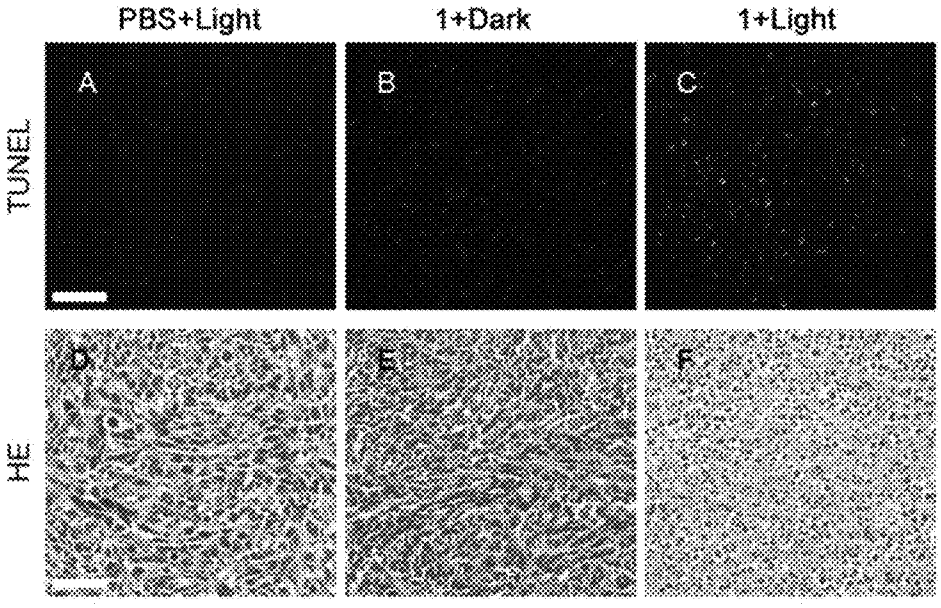
FIG. 19 is TUNEL and HE staining images of tumor tissue sections of 4T1 cell subcutaneous tumors in nude mice in the blank control group administered with PBS and performed with light irradiation (PBS+Light), the group administered with the photosensitized probe and fed in darkness (1+Dark), and the group administered with the photosensitized probe and performed with light irradiation (1+Light), provided by Example 17.

Result Analysis:

The experimental results of Example 17 are shown in FIGS. 16-19. The in vivo fluorescence imaging is performed at different time points during the photodynamic therapy, and the results are shown in FIGS. 16-17. The body weight and tumor volume of nude mice are recorded after the photodynamic therapy, and results are shown in FIG. 18. After the photodynamic therapy, the tumor tissues are sectioned and stained with TUNEL and HE, and the results are shown in FIG. 19.

FIG. 16 is in vivo fluorescent images of nude mice with 4T1 cell subcutaneous tumor treated with (E)-4-(2-(5-methoxy-1H-indole-3-)vinyl)-1-methylquinolinium iodide during and after the photodynamic therapy. Part A of FIG. 16 is the in vivo fluorescent image of the PBS blank control and the photosensitized probe 1 of the present application at 0 min during the photodynamic therapy; Part B of FIG. 16 is the in vivo fluorescent image of the PBS blank control and the photosensitized probe 1 of the present application at 3 min during photodynamic therapy; Part C of FIG. 16 is the in vivo fluorescent image of the PBS blank control and the photosensitized probe 1 of the present application at 5 min during photodynamic therapy; Part D of FIG. 16 is the in vivo fluorescent image of the PBS blank control and the photosensitized probe 1 of the present application at 10 min during photodynamic therapy; Part E of FIG. 16 is the in vivo fluorescent image of the PBS blank control and the photosensitized probe 1 of the present application at 10 min after the photodynamic therapy; Part F of FIG. 16 is the in vivo fluorescent image of the PBS blank control and the photosensitized probe 1 of the present application at 20 min after the photodynamic therapy; Part G of FIG. 16 is the in vivo fluorescent image of the PBS blank control and the photosensitized probe 1 of the present application at 30 min after the photodynamic therapy; and Part H of FIG. 16 is the in vivo fluorescent image of the PBS blank control and the photosensitized probe 1 of the present application at 60 min after the photodynamic therapy. It can be seen from Parts A-H of FIG. 16 that with the progress of the photodynamic therapy treatment, the fluorescence intensity of the tumor site of the nude mice increases significantly, and the fluorescence maintains after the treatment, indicating that the cell apoptosis occurs in the tumor. This indicates that with the photosensitized probe 1 of the present application, the therapeutic efficacy can be monitored during and after the photodynamic therapy based on its fluorescence enhancement.

FIG. 17 shows the in vivo fluorescent image of the nude mice of the blank control after light irradiation (Part A of FIG. 17), the nude mice treated with the photosensitized probe 1 after the photodynamic therapy (Part B of FIG. 17), and the nude mice treated with the photosensitized probe 1 without the photodynamic therapy (Part C of FIG. 17). The nude mice of the blank control (Part A of FIG. 17) and that after drug administration without the photodynamic therapy (Part C of FIG. 17) show weak fluorescence at the tumor site, while the nude mice treated with the photosensitized probe 1 after the photodynamic therapy (Part B of FIG. 17) exhibit bright fluorescence at the tumor site. This further indicates that the fluorescence enhancement can be used to monitor the apoptosis of cells during photodynamic therapy, that is, the efficacy of the photodynamic therapy.

FIG. 18 shows body weight curves and tumor growth curves of nude mice with 4T1 cell subcutaneous tumor after the photodynamic therapy. Part A of FIG. 18 shows the changes of body weight of nude mice within 16 days of therapy, and Part B of FIG. 18 shows the changes in tumor volume of nude mice within 16 days of therapy. There is no significant change in the body weight, which indicates that the toxicity of the drug is low. And among all the mice, the tumor growth of mice treated with the photosensitized probe after the photodynamic therapy ("1+Light") is significantly inhibited, indicating the efficacy of photodynamic therapy on tumors is excellent.

FIG. 19 is TUNEL and HE staining images of tumor tissue sections of nude mice with 4T1 cell subcutaneous tumors after photodynamic therapy. Part A of FIG. 19 is a TUNEL staining image of a tumor tissue section of the blank control group; Part B of FIG. 19 is a TUNEL staining image of a tumor tissue section of the group administrated with the photosensitized probe and fed in darkness; Part C of FIG. 19 is a TUNEL staining image of a tumor tissue section of the group administrated with the photosensitized probe and performed with the photodynamic therapy; Part D of FIG. 19 is a HE staining image of a tumor tissue section of the blank control group; Part E of FIG. 19 is a HE staining image of a tumor tissue section of the group administrated with the photosensitized probe and fed in darkness; and Part F of FIG. 19 is a HE staining image of a tumor tissue section of the group administrated with the photosensitized probe and performed with the photodynamic therapy. The fluorescence in Part C of FIG. 19 shows that the tumor died in the apoptosis pathway after the photodynamic therapy, and the HE staining image in Part F of FIG. 19 also shows that the third group of tumor tissues are seriously damaged, which indicates (E)-4-(2-(5-methoxy-1H-indole-3-)vinyl)-1-methylquinolinium iodide can be used as a photosensitizer for effective photodynamic therapy.

Therefore, method of using a photosensitized probe, the (2-(5-alkoxyindole-3-)vinyl) quinolinium, as a targeted and migratable photosensitizer in photodynamic therapy and synchronous efficacy monitoring is provided. According to the present application, (2-(5-alkoxyindole-3-)vinyl) quinolinium is used as a targeted and migratable photosensitizer. Compared with other photosensitizers, (2-(5-alkoxyindole-3-)vinyl) quinolinium has a targeting ability. It can target the mitochondria of the live cells and only exhibits a weak fluorescent signal in mitochondria of live cells. During photodynamic therapy, the mitochondria are destroyed by the reactive oxygen species produced by the photosensitizer molecules, which effectively induce apoptosis of the cells; in this way, the application in the photodynamic therapy is realized. Meanwhile, photosensitizer molecules are released, migrate from the mitochondria and specifically bind to the ribonucleic acid in cytoplasm and nucleolus, exhibiting strong red fluorescent signal after the binding. Therefore, the application in synchronous efficacy monitoring in photodynamic therapy can be realized based on the significantly enhanced fluorescent signal.

In summary, on the one hand, the mitochondrion/ribonucleic acid-targeted and migratable organic small-molecule photosensitized probe provided in the present application can not only induce the apoptotic pathway of mitochondrial damage, but also accelerate the apoptosis of tumor cells within 3 min by binding to RNA, thereby greatly improving the efficacy of tumor photodynamic therapy. On the other hand, real-time monitoring of therapy response and efficacy evaluation can provide guidance for enhancing the efficacy. The development of the targeted and migratable photosensitized probe is of great significance for studies of tumor photodynamic therapy, apoptosis and drug resistance mechanism, and will also provide chemical tool for the mechanism study of cellular reactive oxygen species stress response.

The above are only optional embodiments of the application, and are not used to limit the application. For those skilled in the art, various modifications and changes may be made based on the present application. Any modification, equivalent replacement, and improvement made within the spirit and principle of the present application shall be included in the scope of the claims of the present application.

What is claimed is:

1. A method of using a mitochondrion/ribonucleic acid-targeted and migratable photosensitized probe as a targeted and migratable photosensitizer, the method comprising:

killing live cancer cells in photodynamic therapy, which comprises:

incubating the live cancer cells with the targeted and migratable photosensitizer, wherein the targeted and migratable photosensitizer localizes in mitochondria in the live cancer cells, and irradiating the live cancer cells by light, whereby inducing the targeted and migratable photosensitizer to produce reactive oxygen species to destroy mitochondria of the live cancer cells and induce apoptosis of the live cancer cells;

cell apoptosis assessment and synchronous efficacy monitoring, which comprises:

monitoring a fluorescence of the cancer cells at different time points during the photodynamic therapy; comparing fluorescence intensities at the different time points during the photodynamic therapy to obtain a result of the fluorescence intensity increases significantly compared with that when all probe molecules localize in mitochondria before the photodynamic therapy, and the fluorescence maintains after the photodynamic therapy;

wherein the targeted and migratable photosensitized probe migrates from the mitochondria of resulting cancer cells after apoptosis of the cancer cells and specifically binds to ribonucleic acid in cytoplasm and nucleoli of the resulting cancer cells, whereby the fluorescence enhances significantly and the synchronous efficacy monitoring is realized;

wherein the mitochondrion/ribonucleic acid-targeted and migratable photosensitized probe is (E)-4-(2-(5-methoxy-1H-indole-3-)vinyl)-1-methylquinolinium iodide;

the live cancer cells comprise live HeLa cells or live 4T1 cells.

2. The method according to claim 1, wherein during destruction of the mitochondria of the live cancer cells, mitochondrial membrane potential is reduced.

* * * * *